United States Patent [19]

Kaplan et al.

[11] Patent Number: 4,946,689
[45] Date of Patent: Aug. 7, 1990

[54] CONCENTRATED, STABILIZED CIS-DIAMMINEDINITRATOPLATINUM SOLUTIONS FOR CONVERSION TO CISPLATIN

[75] Inventors: Murray A. Kaplan, Syracuse; Robert K. Perrone, Liverpool; Joseph B. Bogardus, Manlius; Kenneth W. Douglas, Sr., Mexico, all of N.Y.

[73] Assignee: Bristol-Myers Company, New York, N.Y.

[21] Appl. No.: 275,489

[22] Filed: Nov. 23, 1988

[51] Int. Cl.[5] .............................................. A61K 33/24
[52] U.S. Cl. .................................................. 424/649
[58] Field of Search ................................ 424/131, 649

[56] References Cited

U.S. PATENT DOCUMENTS

| | | | |
|---|---|---|---|
| 4,273,755 | 6/1981 | Rhoda et al. | 424/131 |
| 4,310,515 | 1/1982 | Granatek et al. | 424/131 |
| 4,322,391 | 3/1982 | Kaplan et al. | 424/209 |
| 4,339,437 | 7/1982 | Rosenberg et al. | 424/131 |
| 4,451,447 | 5/1984 | Kaplan et al. | 424/131 |

OTHER PUBLICATIONS

Cleare et al., *Bioinorg. Chem.*, 2:187–210, (1973).
Aggarwal et al., *Cancer Chemother. Pharmacol.*, 4:249–258, (1980).
Boreham et al., *Aust. J. Chem.*, 34:659–664, (1981).
Faggiani et al., *J. of the American Chemical Society*, 99:3 (1977) discloses the crystalline structure and vibrational.
Lippert et al., *Inorganic Chemistry*, vol. 10, 1525 (1977).
King, *Journal of Chemical Society*, (1938), 1338–1346.

*Primary Examiner*—Jerome D. Goldberg
*Attorney, Agent, or Firm*—Mollie M. Yang

[57] ABSTRACT

The invention relates to chemically stable, concentrated solutions of cis-diamminedinitratoplatinum which are pH-stabilized with nitric acid and are readily convertible to parenteral cisplatin solutions by addition of sources of chloride ion.

2 Claims, No Drawings

CONCENTRATED, STABILIZED CIS-DIAMMINEDINITRATOPLATINUM SOLUTIONS FOR CONVERSION TO CISPLATIN

BACKGROUND OF THE INVENTION

1. Field of the Invention

The present invention relates to a stable concentrated aqueous solution of cis-diamminedinitratoplatinum and its use in the preparation of stablized aqueous injectable solutions of cisplatin.

2. Description of the prior Art

The platinum compounds are a unique group of compounds in the antineoplastic group of agents. They were first noted to have an antibiotic effect by Rosenberg and his colleagues in 1965 [Rosenberg, B. et al, *Nature* (London) 205, 698–699 (1965)] and subsequently found by Rosenberg and his colleagues to be potent antitumor agents in animals [Rosenberg, B. et al, *Nature* (London) 222, 385–386 (1969)].

Structurally, they represent a complex formed by a central atom of platinum and surrounded by various arrangements of chlorine atoms or ammonia groups in either a cis or trans planar relationship. Two of the more commonly studied platinum compounds are diagrammed below:

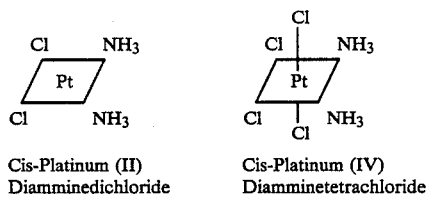

Cis-Platinum (II) Diamminedichloride    Cis-Platinum (IV) Diamminetetrachloride

As can be seen, the compound cis-platinum (II) diamminedichloride has all its chloro and amino groups in a single plane. This compound, now know by the United States Adopted Name (USAN) cisplatin, has been synthesized according to the following reaction:

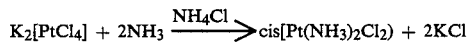

[see Kauffman, G. B. et al, in *Inorganic Synthesis*, J. Kleinberg (Ed.), pages 289–245, McGraw-Hill Book Co., Inc., New York 1963].

Breusova-Baidala, Y. G. et al, in *Akademia Nauk SSSR*, No. 6, pp. 1239–1242 (June 1974), discuss the slow isomerization of cis-platinum (II) diamminedichloride in aqueous solution to the trans form.

Reishus, J. W. and Martin, D. S., in *Journal of the American Chemical Society*, 83, 2457–2462 (1961), describe the acid hydrolysis of cisplatin at 25° C. and 35° C. These studies were conducted in aqueous solutions at concentrations of $1.5\times10^{-3}$ M, $2.5\times10^{-3}$ M and $5.0\times10^{-3}$ M, which correspond to 0.45, 0.75 and 1.5 mg/ml, respectively. The authors state that there was some ambiguity in locating the origin (i.e., "zero point") for the hydrolysis curves because the samples required from 10 to 30 minutes to dissolve completely even at those low concentrations.

Rozencweig, M. et al, in *Annals of Internal Medicine*, 86, 808–812 (1977), review the results of various pre-clinical and clinical investigations of the use of cisplatin in experimental tumors in animals as well as various types of human tumors. They point out that the investigational drug, available to qualified investigators through the Investigational Drug Branch of the Cancer Therapy Evaluation Program of the National Cancer Institute, was supplied as a white lyophilized powder in vials containing 10 mg of cisplatin, 90 mg of sodium chloride, 100 mg of mannitol (U.S.P.) and hydrochloric acid for pH adjustment. When reconstituted with 10 ml of sterile water for injection (U.S.P.). each ml of the resulting solution would contain 1 mg of cisplatin, 10 mg of mannitol and 9 mg of NaCl.

Talley, R. W. et al, in *Cancer Chemotherapy Reports*, 57, 465–471 (1973), describe the results of their Phase I clincal study of the use of cisplatin in the treatment of 65 human patients with a wide variety of neoplasms. As in the preceding publication, the drug was supplied to them by the National Cancer Institute in vials containing 10 mg of cisplatin, 90 mg sodium chloride and 100 mg of mannitol, for reconstitution with 10 ml of sterile water.

Certain information concerning the chemistry and pharmaceutical formulation of cisplatin is given on pages 1–5 and 31–32 of the publication entitled "CLINICAL BROCHURE, CIS-PLATINUM (II) DIAMMINEDICHLORIDE (NSC-119875)", H. Haldelsman et al, Investigational Drug Branch, Cancer Chemotherapy Evaluation Program, Division of Cancer Treatment, National Cancer (Revised August 1974). Pages 31 and 32 thereof concern the formulation of cisplatin supplied gratis by the N.C.I. to clinicians for their clinical evaluation in the chemotherapy of cancer and read as follows:

PHARMACEUTICAL DATA SHEET

NSC-119875 Cis-Diamminedichloroplatinum (II)

Dosage Formulation
 10 mg./vial The contents of each 20 ml. flint vial appears as an off-white lyophilized cake. Each vial contains 10 mg. of NSO-119875; 90 mg. of Sodium Chloride; 100 mg. of Mannitol and Hydrochloric acid for pH adjustment Solution Preparation
 10 mg./vial When reconstituted with 10 ml. of Sterile Water for Injection, USP, each ml. of the resulting solution will contain 1 mg. of NSC-119875, 10 mg. of Mannitol, and 9 mg. of Sodium Chloride having a pH range of 3.5–4.5.

Storage The dry, unopened vials should be stored at refrigeration temperatures (4°–8° C.)

Stability Intact vials have a provisional stability of one year when stored at refrigeration temperature (4°–8° C.). Stability recommendations may be adjusted pending completion of a two-year shelf-life study. Reconstitution as recommended results in a pale, yellow solution which is stable for not more than one hour at room temperature (22° C.) when exposed to normal room illumination and not more than eight hours at room temperature (22° C.) when protected from light. Reconstituted solutions may form a precipitate after one hour at refrigeration temperature (4°–8° C.).

Caution The lyophilized dosage formulations contain no preservatives and therefore it is advised to discard solutions eight hours after reconstitution.

Current, commercial ready-to-use aqueous parenteral dosage forms of cisplatin generally contain 0.5 or 1.0 mg/ml of activity, at a pH range of approximately 2.5–4, with requirements for storage at controlled room temperature, e.g., 15°–25° C. Of these, the more practical formulations are those at 0.5 mg/ml. At concentrations above approximately 0.6 mg/ml, crystallization of cisplatin is noted upon cooling to less than 10° C. or upon freezing-thawing. The crystals are slow to dissolve, even with warming to 45° C.

When stored at elevated temperatures, e.g. 37°–6° C., none of the present commercially available formulations demonstrate acceptable stabilities. Considerable quantities of trichloroammineplatinum-II (TOAP) and other degradation products are formed over relatively short periods (2–4 weeks) of time. Although commercially accepted, these dosage forms are far from ideal. Because of low concentrations of cisplatin in the ready to use solutions, large vials and volumes resulting in costly storage and shipping are required for therapeutic requirements, i.e. up to 200 ml for 100 mg of cisplatin.

SUMMARY OF THE INVENTION

There is provided by the present invention a stable aqueous solution of cis-diamminedinitratoplatinum having a concentration of cis-diamminedinitratoplatinum between about 1 and 100 mg/ml and an appropriate amount of a nontoxic, pharmaceutically and therapeutically acceptable acid, preferably nitric acid. This acid is necessarily present in an amount sufficient so that upon conversion of the cis-diamminedinitratoplatinum solution to a stable solution of cisplatin by the addition of sodium chloride, the resultant cisplatin solution possesses a pH in the range about 2.5 to less than 4.5, preferably about 2.5 to 3.8.

DETAILED DESCRIPTION OF THE INVENTION

The instant invention relates to a ready-to-use concentrated, aqueous solution of cis-diamminedinitratoplatinum (DDNp) Which is diluted With 0.5% to >5% sodium chloride solution to convert DDNp into a ready-to-use intravenous aqueous solution of cisplatin by the reaction:

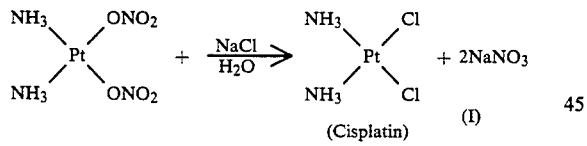

(Cisplatin)

DDNP actually exists in aqueous solution as (cis-Pt(NH$_3$)$_2$—(H$_2$O)$_2$$^{+2}$ NO$_3$$^-$)

It has been discovered in the instant invention that an essential element of the DDNP solution is a sufficient amount of a pharmaceutically and therapeutically acceptance and, preferably nitric acid, such that the final cisplatin aqueous solution upon subsequent dilution with a chloride ion source possesses a pH of less than 4.5, preferably between 2.5 and 4.5, most preferably between 2.5 and 3.8. The low pH of the DDNP and cisplatin solutions ensures the quantitative conversion of DDNP to cisplatin while avoiding the formation of undesirable relatively toxic by-products such as dimers, trimers and varied aquated species.

The pharmaceutically and therapeutically acceptable nitric acid which is utilized to stabilize the DDNP solution surprisingly displays superior stabilizing characteristics than other acids which were tested such as acetic acid and lactic acid.

The cis-diamminedinitratoplatinum (DDNP) which is used in the instant invention to prepare the stable DDNP solution is itself readily prepared in accordance by a variety of known techniques. The following procedure exemplifies one known technique:

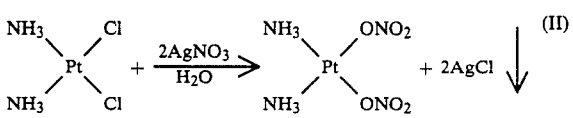

Procedure

MW: Cisplatin = 300.2
MW: AgNO$_3$ = 169.87

$$\frac{1.0}{30.2} = \frac{X}{(169.87)_2} = 1.132 \text{ g of AgNO}_3 \text{ is equivalent to } 1 \text{ g of Cisplatin to form the dinitrate.}$$

1. Slurry 1 g of Cisplatin in 50 mL of deionized water, in-the-dark, at 20°–30° C.
2. Add, over a 5 minute interval, 1.25 g of AgNO$_3$, (2.1 molar equivalents).
3. Rapidly stir the mixture in the dark (20°–30° C.) for 2 hours.
4. Raise the temperature to 45°–55° C. over a 0.5 hour interval. Stir rapidly. Continue stirring at 45°–55° C. for 1 hour and ambiently for 24 hours, all in-the-dark.
5. Collect the precipitated AgCl by vacuum filtration on a suitable, fine, scintered glass filter funnel or 0.22 micron pore size membrane filter.
6. Wash the AgCl filter-cake with 10 mL of deionized water. Add the wash to the filtrate.
7. Concentrate the filtrate to approximately 10–20 mL in a "Rotovac" (bath-temperature at 50°–60° C.).
8. Remove any precipitate which may have formed by filtration through a suitable, scintered fine glass funnel or 0.22 micron pore size membrane filter.
9. Concentrate the filtrate to a crystalline residue in a "Rotovac" (bath-temperature at 50°–60° C.)
10. Slurry the crystals in 50 mL of methanol for 1 hour (any excess AgNO$_3$ which may be present is extracted into the methanol).
11. Collect the crystals by vacuum filtration on a suitable scintered fine glass filter-funnel.
12. Wash the crystals with 20 mL of methanol, 25 mL of ether and vacuum dry at 50° C. —P$_2$O$_5$—3 hours. Expected yield of cis-diamminedinitratoplatinum-II is 0.85–0 95 g.

The stable DDNP solution of the present invention is prepared under aseptic conditions by mixing the above prepared DDNP with a stabilizing amount of concentrated HNO$_3$ preferably at a pH of 1.5 to 8.0, for instance 4 mM at a pH of 2.4, to 50 mM at a pH of 1.5 and water in the following preferred ratio:

| Ingredient | Per mL | Specific Example |
|---|---|---|
| DDNP | 1 to 100 mg | 12.0 mg |
| Concentrated HNO$_3$* | 0.1–2.0 mcL*[1] | 0.24 mcL |
| Water U.S.P. | q.s. to 1 mL | 1.00 ml |

*69–71% w/w on label, or approximately 16M.
*[1]Required to yield a final pH of 2.5–4.5 after conversion of DDP to Cisplatin with 0.9% NaCl. A pH of up to 7.0 is acceptedly attainable by use of 5–10% NaCl solution with less buffering HNO$_3$ present.

The mixture is sterilized by filtration and placed in amber vials which ar sealed with suitable rubber stoppers and aluminum closures.

The above produced stable aqueous solution of DDNp and HNO$_3$ can readily possess a DDNP concentration of up to 1 to 100 mg/ml. Before administration to a patient, these DDNP solutions must be diluted with Normal Saline Solution (NSS) (0.9% NaCl) in a ratio of DDNP solution/NSS of at least 1/10 or with up to or greater than 5% NaCl solution to yield 1 mg/ml or less of cisplatin solution. Conversion of DDNP solution to cisplatin by reaction formula (I) takes approximately 1 hour. 0 9% sodium Chloride Injection U.S.P. is recommended for any further dilutions.

The acid stabilized concentrated solutions of DDNP are converted to 1 mg/ml or less of cisplatin solutions by dilution with appropriate volumes of 0.5-10% NaCl solutions. The use of higher concentrations of NaCl solutions, such as 5%, forces the equilibrium to the conversion reaction of DDNP to cisplatin to greater than 99 percent conversion.

The concentrated aqueous solutions of DDNP utilized in the instant invention for subsequent conversion to parenteral cisplatin are obtainable in concentrations in the range of 1 to 100 mg/ml. Furthermore, concentrations of 10 to 50 mg/ml of the DDNP solutions display no precipitation at temperature ranges of 4° to 25° C. The DDNP solutions display no precipitation upon repeated freezing ($-10°$ to $-60°$ C.) and thawing (25° to 45° C.). In view of generally unstable platinum complexes, the instant DDNP solutions are unexpectedly stable even at elevated temperatures wherein no significant amounts of degradation products are evident for at least 2 months at 56° C. or 1 year at 25° C.

Although the conversion of the stable DDNF solution to cisplatin has been displayed with NaCl solutions it should be appreciated that other chloride ion containing solutions can be employed. The chloride ion may be provided by the addition of hydrochloric acid, a nontoxic pharmaceutically metallic halide such as sodium chloride, potassium chloride, calcium chloride or magnesium chloride, or the hydrochloric acid addition salt of a nontoxic pharmaceutically acceptable tertiary amine such as triethylamine, or by mixtures thereof. The preferred source of chloride ion is sodium chloride.

Preferably the solution contains from about 1 to about 100 mg of DDNP per ml and most preferably from about 10 to about 50 mg/ml. The nontoxic, pharmaceutically acceptable source or chloride ion preferably is present in a concentration of at least about two equivalents per equivalent of DDNP in the solution. Concentrations as high as 50 equivalents or more of chloride ion per equivalent of DDNP may be utilized, depending on the DDNP concentration, the percentage of water present and the particular source of chloride ion, but such high concentrations of chloride ion usually may not be necessary. It will be appreciated by those skilled in the art that it is preferable to maintain the produced cisplatin solutions in an excess of chloride ion to stabilize the cisplatin against subsequent degradation. In the situation set forth above, the use of higher equivalents of chloride ion per equivalent of DDNP could be obtained by the use of hydrochloric acid as the source of chloride ion, but this might give a solution having an undesirably high acidity, i.e., low pH. We have found that excessively acidic solutions are somewhat less stable than more moderately acidic solutions. The pH range of the solutions preferably is from about 2.5 to about 4.5 when 0.9% saline solution is used, however, use of 5-10% NaCl solution allows for a pH of up to 7.0 without significant from about 2 to about 10 equivalents of chloride ion per equivalent of DDNP, and most preferably from about 4 to about 8 equivalents of chloride ion per equivalent of DDNP to ensure complete conversion of DDNP to cisplatin.

It will be appreciated that the concentrated solutions of DDNP provided by the present invention will require lower shipping, storage and other costs per unit dose when compared to the known aqueous solutions of cisplatin. Although the know lyophilized solid form of cisplatin also has lower shipping and storage costs, that saving is more than offset by the time and expenses involved in lyophilization.

As displayed in reaction formula I the DDNP solutions which are converted to cisplatin solutions, to which mannitol is optionally added, are equivalent to present commercial solutions with two mole equivalents of $NaNO_3$ formed during the reaction. For example, 120 mg of DDNP (equivalent to 100 mg of cisplatin) forms 57.79 mg of $NaNO_3$ according to reaction formula I. This amount of $NaNO_3$ formed from a 120 mg dose of DDNP is only approximately 0.8% of the $LD_{50}$ of $NaNO_3$, an insignificant contribution to toxicity.

Although no particular advantage is obtained by their presence, the solutions of this invention may, if desired, contain a customary, physiologically acceptable excipient such as mannitol.

Based on stability studies to date, the predicted stability of the solutions of this invention is in excess of two years at room temperature.

In a preferred embodiment of this invention, the DDNP solutions are sterile and pyrogen-free, and are packaged in sterile, pyrogen-free containers. Such solutions are diluted with, for example, Sterile 0.9% Sodium Chloride Injection, U.S.P. and administered by the intramuscular or intravenous route. A means for sterilizing these solutions is filtration through a sterile, pyrogen-free 0.22 micron membrane filter, using aseptic techniques, under sterile nitrogen pressure. The sterile filtrate is collected in sterile, pyrogen-free containers and is ultimately filled, in the desired amount, into suitable sterile, pyrogen-free vials, stoppered with sterile, pyrogen-free stoppers (preferably teflon coated) and sealed with sterile aluminum seals.

For use in the treatment of cancer, the concentrated DDNP solutions are converted to cisplatin solutions of the desired concentration (typically 1 mg cisplatin per ml) with, for example, Sterile 0.9% Sodium Chloride Injection. U.S.P and used by intramuscular or intravenous injection, or intravenous infusion as known for prior art cisplatin preparations. Currently used dosages with mild to moderately acceptable toxicity are in the range of 60-100 $mg/M^2$ intravenously as a single dose or divided over 3-5 days, to be repeated at 4-week intervals. A dosage of 60 $mg/M^2$ is roughly equal to 1.5 mg/kg which in turn is roughly equal to 105 mg/patient weighing 70 kg. Frequently, use is made of concurrent therapy with other chemotherapeutic agents for best results.

EXAMPLE

A twelve mg/ml DDNP solution was prepared by dissolving 252 mg. of cis-diamminedinitratoplatinum (DDNP) in 21 ml Water for Injection, U.S.P. to which 5 mcl. of $HNO_3$ was added to give a final pH of 2.4. These stable concentrated solutions were each placed in a separate 17 ml. amber vial to protect them from light, stopper with a rubber stopper and sealed with an aluminum cap. These stable concentrated DDNP solutions were stored for a variety of durations ranging from 2 weeks (w) to one year at temperatures ranging from 25° C. to 56° C. The stability of the aqueous DDNP solutions is demonstrated in Table I via the recovery of cisplatin from each DDNP solution. After the displayed storage time each i ml DDNP solution was diluted with 10 ml of Normal Saline Solution (0.9% NaCl) U.S.P and allowed to stand for approximately one hour at the room temperature for each sample. Assays were then performed on each sample for cisplatin and trichloroammineplatinum (TCAP) by high performance liquid chromatography (HPLO). HPLO assays of DDNP solution samples which had been stored for periods ranging from 2 to 8 weeks at 45° to 56° to one year at 25° displayed potency losses ranging from 0 to 4% and TCAP percentages ranging from 0 to 0.4%. Also displayed in Table I are comparative commercial solutions of 0.5 mg/ml of cisplatin at a pH of 4.0 which contained 1.47% of TCAP after four weeks storage and 2.76% of TCAP after 12 weeks storage at 37° C.

TABLE I

Stability of 12 mg/mL Aqueous Solutions of DDNP (pH 2.4)
% Cisplatin Remaining (% TCAP Present)*[1]

| 25° C. year | 37° C. 8W | 37° C. 12W | 45° C. 2W | 45° C. 5W | 45° C. 8W | 56° C. 2W | 56° C. 5W | 56° C. 8W |
|---|---|---|---|---|---|---|---|---|
| 100.6(0) | 101.6(0.1) | 101.6(0) | 100.2(0) | 97,100(0) | 97,98(0) | 100.2(0) | 97.1(0.28) | 96,97(0.2,0.4) |
| Commercial Solution, 0.5 mg/mL Cisplatin pH 4.0 | 4W 98.6(1.47) | 92.7(2.76)*[2] | | | | | | |

*[1]Samples diluted 1/10 with 0.9% NaCl to yield 1 mg/mL of cisplatin (1 hour holding). Assays for cisplatin and TCAP (trichloroammineplatinum) obtained via HPLC.
4.5% activity unaccounted (transplatin not present)

What is claimed is:

1. A sterile, stable concentrated aqueous solution of cis-diamminedinitratoplatinum, said solution consisting essentially of cis-diamminedinitratoplatinum in a concentration between about 1 and 100 mg/ml and nitric acid in an amount ranging from 0.1 to 2.0 mcL per ml of said solution.

2. A sterile, stable concentrated aqueous solution of cis-diamminedinitratoplatinum having a pH ranging from 1.5 to 3.0, said solution consisting essentially of cis-diamminedinitratoplatinum in a concentration between about 10 and 100 mg/ml and a pH stabilizing amount of nitric acid.

* * * * *